United States Patent
Wu et al.

(10) Patent No.: US 9,847,242 B2
(45) Date of Patent: Dec. 19, 2017

(54) APPARATUS AND METHOD FOR ALIGNING TWO PLATES DURING TRANSMISSION SMALL ANGLE X-RAY SCATTERING MEASUREMENTS

(71) Applicant: Industrial Technology Research Institute, Chutung, Hsinchu County (TW)

(72) Inventors: Wen-Li Wu, Chutung (TW); Yen-Song Chen, Chutung (TW); Wei-En Fu, Chutung (TW); Yun-San Chien, Chutung (TW); Hsin-Chia Ho, Chutung (TW)

(73) Assignee: Industrial Technology Research Institute, Chutung (TW)

( * ) Notice: Subject to any disclaimer, the term of this patent is extended or adjusted under 35 U.S.C. 154(b) by 136 days.

(21) Appl. No.: 14/582,749

(22) Filed: Dec. 24, 2014

(65) Prior Publication Data

US 2016/0187267 A1 Jun. 30, 2016

(51) Int. Cl.
*G01N 23/201* (2006.01)
*H01L 21/68* (2006.01)

(52) U.S. Cl.
CPC ........ *H01L 21/68* (2013.01); *G01N 2223/054* (2013.01); *G01N 2223/6116* (2013.01)

(58) Field of Classification Search
CPC ..... G01N 2223/054; G01N 2223/6116; G01N 23/201; G01N 23/203; G01N 15/0205; G01N 2015/0846; G01N 2015/086; G01N 23/00; G01N 23/04; G01N 23/207; G01N 2500/02; H01L 2924/0002; H01L 2924/00; H01L 23/293; H01L 23/295; B29C 47/0014; B29C 47/0021; B29C 47/60; G21K 1/025; G21K 2207/005;
(Continued)

(56) References Cited

U.S. PATENT DOCUMENTS 7,481,579 B2   1/2009  Yokhin et al.
7,600,916 B2  10/2009  Yokhin et al.
(Continued)

FOREIGN PATENT DOCUMENTS

CN   103430297 A       12/2013
JP   2007305971 A  *  11/2007  ......... G03F 7/70633
(Continued)

OTHER PUBLICATIONS

JP 2007-305971 English Abstract.
(Continued)

*Primary Examiner* — Irakli Kiknadze
(74) *Attorney, Agent, or Firm* — McCarter & English, LLP; Yu Lu (57) ABSTRACT

The disclosure provides an apparatus for aligning first and second plates that are parallel to each other and have the same orientation. The apparatus includes a detector that detects composite small-angle X-ray scattering emitted from patterns of the first and second plates that are perpendicularly impinged by X-ray, and a moving unit that aligns the first and second plates according to a composite amplitude distribution of the composite small-angle X-ray scattering. Therefore, the first and second plates are aligned to each other accurately.

11 Claims, 7 Drawing Sheets

(58) Field of Classification Search
CPC ....... C08J 2353/00; C08J 5/00; G03F 7/0002; H05G 1/10
USPC .......... 378/154, 62, 70, 85; 250/384, 370.09
See application file for complete search history.

(56) References Cited

U.S. PATENT DOCUMENTS

| | | | | |
|---|---|---|---|---|
| 8,339,595 | B2* | 12/2012 | Den Boef | G03F 7/70633 356/237.5 |
| 8,687,766 | B2* | 4/2014 | Wormington | G01N 23/207 378/70 |
| 2012/0153177 | A1* | 6/2012 | Iwakiri | A61B 6/4291 250/370.09 |
| 2012/0281814 | A1 | 11/2012 | Yokhin et al. | |
| 2014/0067316 | A1* | 3/2014 | Ishibashi | G01N 23/201 702/150 |
| 2015/0117610 | A1 | 4/2015 | Veldman et al. | |

FOREIGN PATENT DOCUMENTS

| | | |
|---|---|---|
| JP | 2007305971 A | 11/2007 |
| JP | 2009049051 A | 3/2009 |
| JP | 2011507264 A | 3/2011 |
| JP | 2012085995 A | 5/2012 |
| JP | 2012130451 A | 7/2012 |

OTHER PUBLICATIONS

JP 2009-049051 English Abstract.
JP 2011-507264 English Abstract.
JP 2012-085995 English Abstract.
Office Action dated Aug. 1, 2016 in JP 2015-212355.
Wang et al., "Small angle X-ray scattering measurements of spatial dependent linewidth in dense nanoline gratings," *Thin Solid Films*, 517:5844-5847 (2009).
Wu et al., "Small angle neutron scattering measurements of nanoscale lithographic features," *J. Appl. Phys.*, 88(12):7298-7303 (2000).
CN 103430297A English abstract.
JP2012130451 English abstract.
JP2015212355 Office action dated Mar. 13, 2017.

* cited by examiner

APPARATUS AND METHOD FOR ALIGNING TWO PLATES DURING TRANSMISSION SMALL ANGLE X-RAY SCATTERING MEASUREMENTS

TECHNICAL FIELD

The technical field relates to alignment techniques, and, more particularly, to an apparatus for aligning two plates during transmission small angle X-ray scattering measurements and a related method.

BACKGROUND OF THE INVENTION

Semiconductor technology develops rapidly. 10-nanometer, or less, fabrication process is ready to come to the market. A semiconductor product is fabricated by tens, or hundreds of steps. Errors will accumulate. Therefore, precise alignment is an important issue.

Mechanical alignment and optical alignment are two popular ways to align two wafers. Mechanical alignment takes the notch or flat of a wafer as a basis for alignment, and uses special pins to align the wafer. Optical alignment, e.g., direct alignment, allows visible or infrared light to pass wafers, and uses optical instruments to align the wafers by reference to positioning marks disposed thereon.

However, these alignment mechanisms are not qualified to address the 10-nanometer fabrication process.

SUMMARY OF THE INVENTION

The disclosure provides an apparatus for aligning a first plate and a second plate that are parallel to each other and have the same orientation, the apparatus comprising: a detector that detects composite small-angle X-ray scattering emitted from patterns of the first and second plates that are perpendicularly impinged by X-ray; and a moving unit that aligns the first and second plates according to a composite amplitude distribution of the composite small-angle X-ray scattering.

The disclosure further provides a method for aligning a first plate and a second plate that are parallel to each other and have the same orientation, the method comprising: detecting composite small-angle X-ray scattering emitted from patterns of the first and second plates that are perpendicularly impinged by X-ray; and aligning the first and second plates according to a composite amplitude distribution of the composite small-angle X-ray scattering.

BRIEF DESCRIPTION OF THE DRAWINGS

The disclosure can be more fully understood by reading the following detailed description of the preferred embodiments/examples, with references made to the accompanying drawings.

DETAILED DESCRIPTION OF THE INVENTION

The following embodiments are described in sufficient detail to enable those skilled in the art to make and use the disclosure. It is to be understood that other embodiments would be evident based on the disclosure, and that system or mechanical changes may be made without departing from the scope of the disclosure.

In the following description, numerous specific details are given to provide a thorough understanding of the disclosure. However, it will be apparent that the disclosure may be practiced without these specific details. In order to avoid obscuring the disclosure, some well-known mechanisms and system configurations are not disclosed in detail.

The drawings showing embodiments of the architecture are semi-diagrammatic and not to scale and, particularly, some of the dimensions are for clarity of presentation and are shown exaggerated in the drawings. Similarly, although the views in the drawings for ease of description generally show similar orientations, this depiction in the drawings is arbitrary for the most part. Generally, the disclosure can be operated in any orientation.

The disclosure is described by the following specific embodiments and examples. Those with ordinary skills in the arts can readily understand the other functions of the disclosure after reading the disclosure of this specification. The disclosure can also be implemented with different embodiments and examples. Various details described in this specification can be modified based on different viewpoints and applications without departing from the scope of the disclosure.

Transmission small-angle X-ray scattering (tSAXS) has been identified as a potential solution for measuring nano-scale features by interrogating structures with sub-nanometer wavelength X-ray radiation. Most relevant parameters describing critical dimensions (CDs) of nano-scale features are pitch, pitch variations, side wall angle, line edge roughness, line width roughness and so forth. Based on the spacing of diffraction peaks, the parameter (pitch) can be extracted from the tSAXS scattering pattern. The geometric form factors of a structure can be extracted from the envelope function of the scattering intensity. In addition to the CDs of a structure, tSAXS has been used to successfully characterize LER, pitch walk, non-planar film thicknesses on sidewalls and complicated profiles of a memory structure that requires a 6-trapezoid model. Since the X-ray wavelength is still much smaller than the feature size of today's nano-scale structure, the tSAXS technique will stay as a viable CD metrology in the future. Actually the applicability of tSAXS will improve at future technology nodes where more densely packed features or an ever decreasing pitch will result in widely apart scattering peaks; thus, more readily detectable via tSAXS. Additionally, it avoids the issues related to optical properties, e.g. n and k, their wavelength and size dependences since tSAXS is based on classical X-ray elastic scattering, the observed scattering intensity depends only on variation in local electron density $\rho$.

The disclosure provides a method for aligning nano-scale, for example, first and second plates 1 and 2 (e.g., wafers) during transmission small angle X-ray scattering measurements, the first and second plates 1 and 2 being parallel to each other and having the same orientation.

Figure 1:
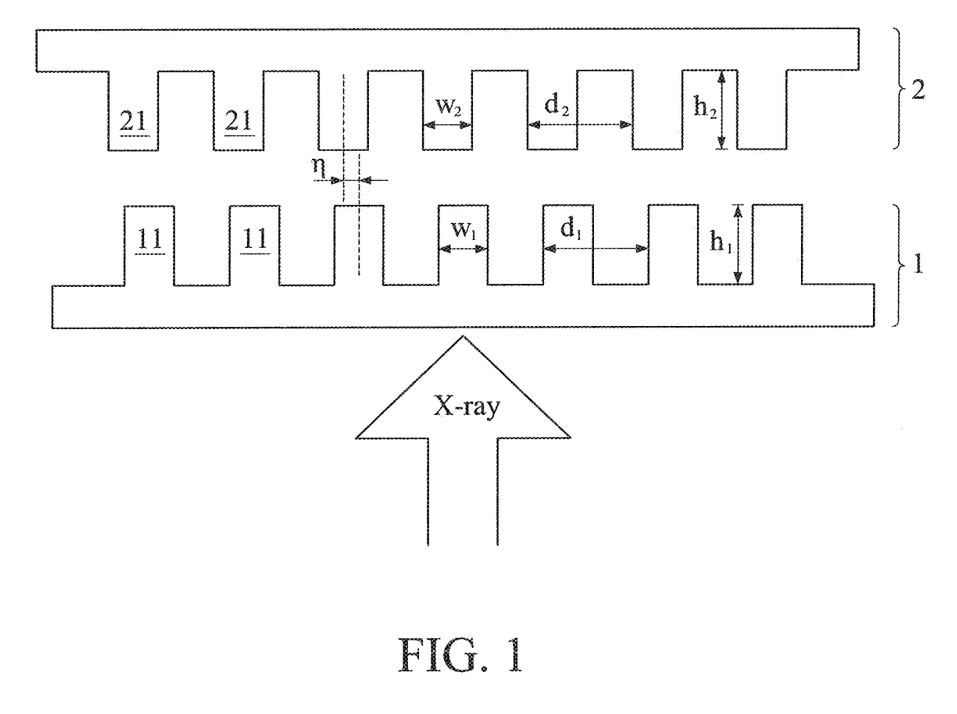
FIG. 1 shows first and second plates to be aligned by a method and an apparatus according to the disclosure.

As shown in FIG. 1, the first plate 1 has a plurality of patterns (or marks) 11, two adjacent ones of the patterns 11 are spaced at a pitch d1, and each of the patterns 11 has a width w1 and a height h1; the second plate 2 also has a plurality of patterns (or marks) 21, two adjacent ones of the patterns 21 are spaced at an pitch d2, and each of the patterns 21 has a width w2 and a height h2; and the first plate 1 and the second plate 2 are misaligned by a misalignment amount η.

For simplicity, in an embodiment the width w1, the height h1 and the pitch d1 are equal to the width w2, the height h2 and the pitch d2, respectively.

Assuming that a distance between the first and second plates 1 and 2 is less than a coherence length of X-ray, and X-ray is impinged onto the first plate 1 and then passes through the second plate 2 perpendicularly, composite small-angle X-ray scattering I(q) emitted from the patterns 11 and 21 of the first and second plates 1 and 2 satisfies the following equation:

$$I(q) \propto \Delta b_{11}^2 \times F_{21}^2(q) + \Delta b_{21}^2 \times F_{21}^2(q) + 2\Delta b_{11} b_{21} \cos(q\eta)|F_{11}(q)F_{21}(q)|,$$

where $\Delta b_i$ represents the contrast factor and $\Delta b_i = h_i \times \rho_i$, and $F_i$ represents the Fourier transform of the corresponding pattern structures.

Figure 2:
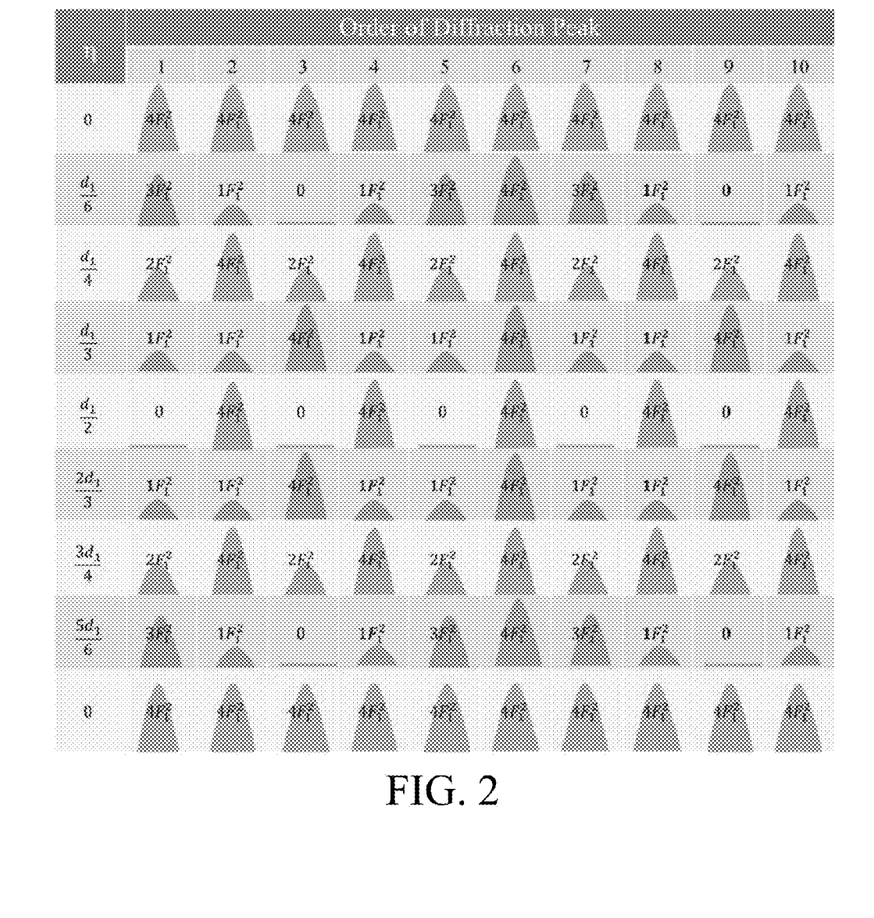
FIG. 2 shows small-angle X-ray scattering of the two plates with a misalignment amount that are impinged by X-ray.

Assuming the pattern 11 is identical to the pattern 21, i.e., $d_1 = d_2$, $w_1 = w_2$ and $h_1 = h_2$, FIG. 2 shows a composite amplitude distribution of the composite small-angle X-ray scattering I(q) for a variety of η. It is clear from the equation and FIG. 2 that the interaction term, i.e., $2\Delta b_{11} b_{21} \cos(q\eta)|F_{11}(q)F_{21}(q)|$, dominates the composite small-angle X-ray scattering I(q). As $\eta = 0$, $d_1/6$, $d_1/4$, $d_1/3$, $d_1/2$, $2d_1/3$, $3d_1/4$ or $5d_1/6$, the composite small-angle X-ray scattering I(q) has different composite amplitude distribution; namely, the diffraction peaks have different intensities or combination thereof. For instance, as $\eta = 0$, the diffraction peaks have the greatest intensities. Therefore, the first and second plates 1 and 2 can be aligned by reference to the composite amplitude distribution of the composite small-angle X-ray scattering I(q).

FIGS. 3A-3E illustrate a method and an apparatus 3 for aligning the first and second plates 1 and 2 during transmission small angle X-ray scattering measurements according to the disclosure. The apparatus 3 comprises an X-ray source 31, a detector 32, and a moving unit 33.

Figure 3A:
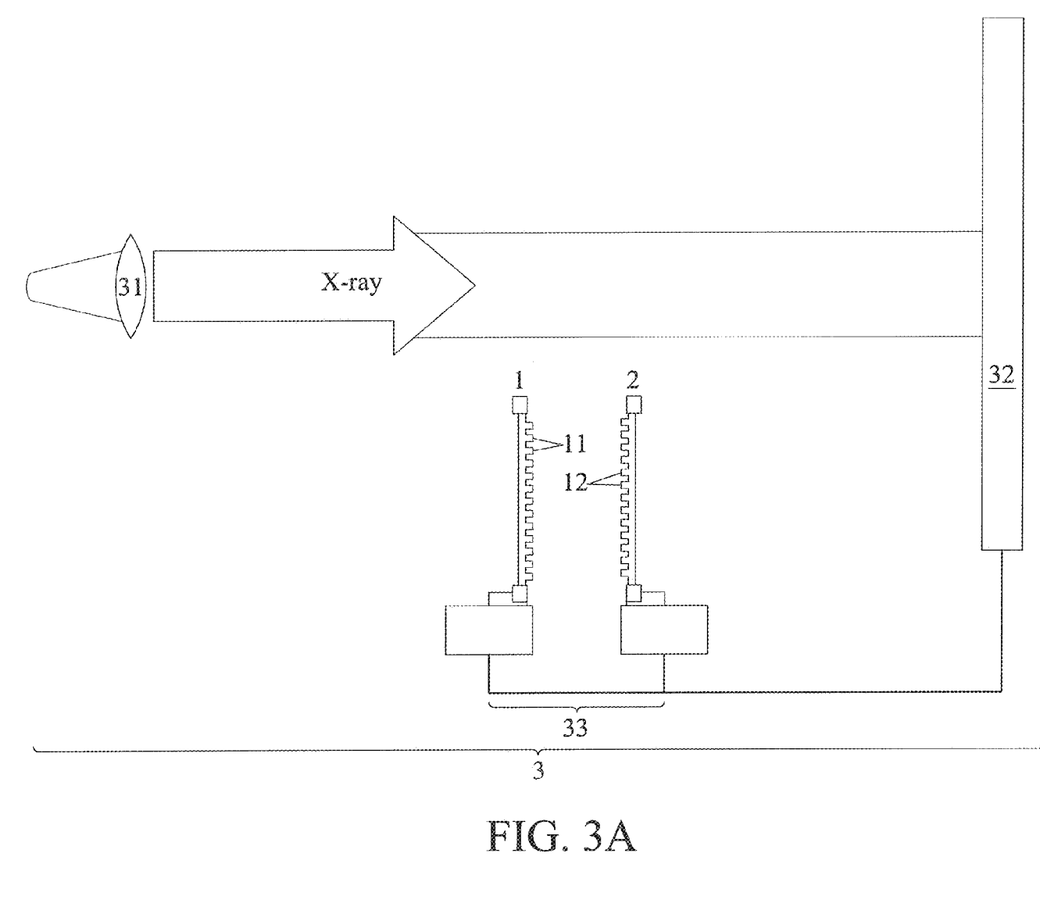
FIGS. 3A-3E illustrate a method and an apparatus for aligning first and second plates during transmission small angle X-ray scattering measurements according to the disclosure.

As shown in FIG. 3A, the X-ray source 31 impinges directly onto the detector 32.

Figure 3B:
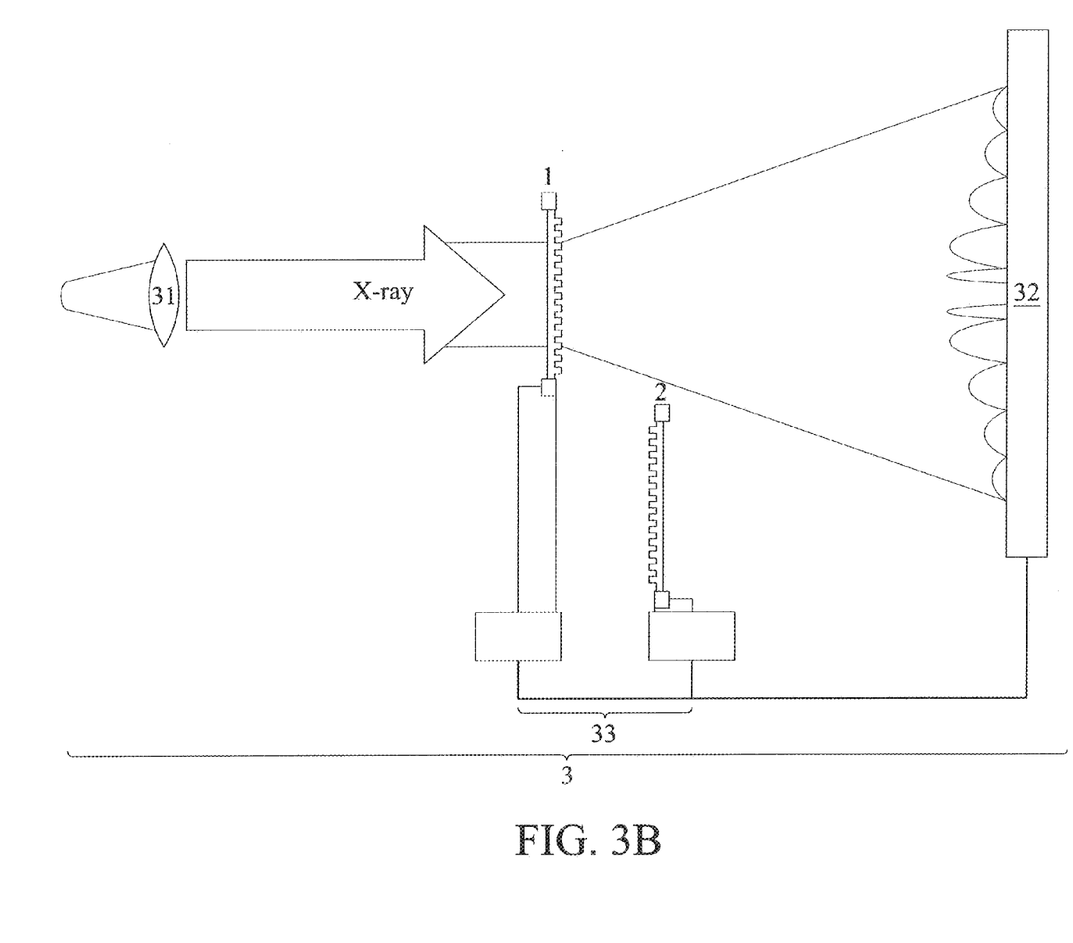

As shown in FIG. 3B, the moving unit 33 raises the first plate 1 to an extent that the X-ray impinges on and passes through the first plate 1. The detector 32 detects first small-angle X-ray scattering emitted from the pattern 11 of the first plate 1. The moving unit 33 tilts the first plate 1 according to a first amplitude distribution of the first small-angle X-ray scattering until the first plate 1 is perpendicular to the X-ray.

The detector 32 then detects a second small-angle X-ray scattering emitted from the pattern 11 of the first plate 1 that is perpendicularly impinged by the X-ray. The moving unit 33 also rotates the first plate 1 according to a second amplitude distribution of the second small-angle X-ray scattering.

Figure 3C:
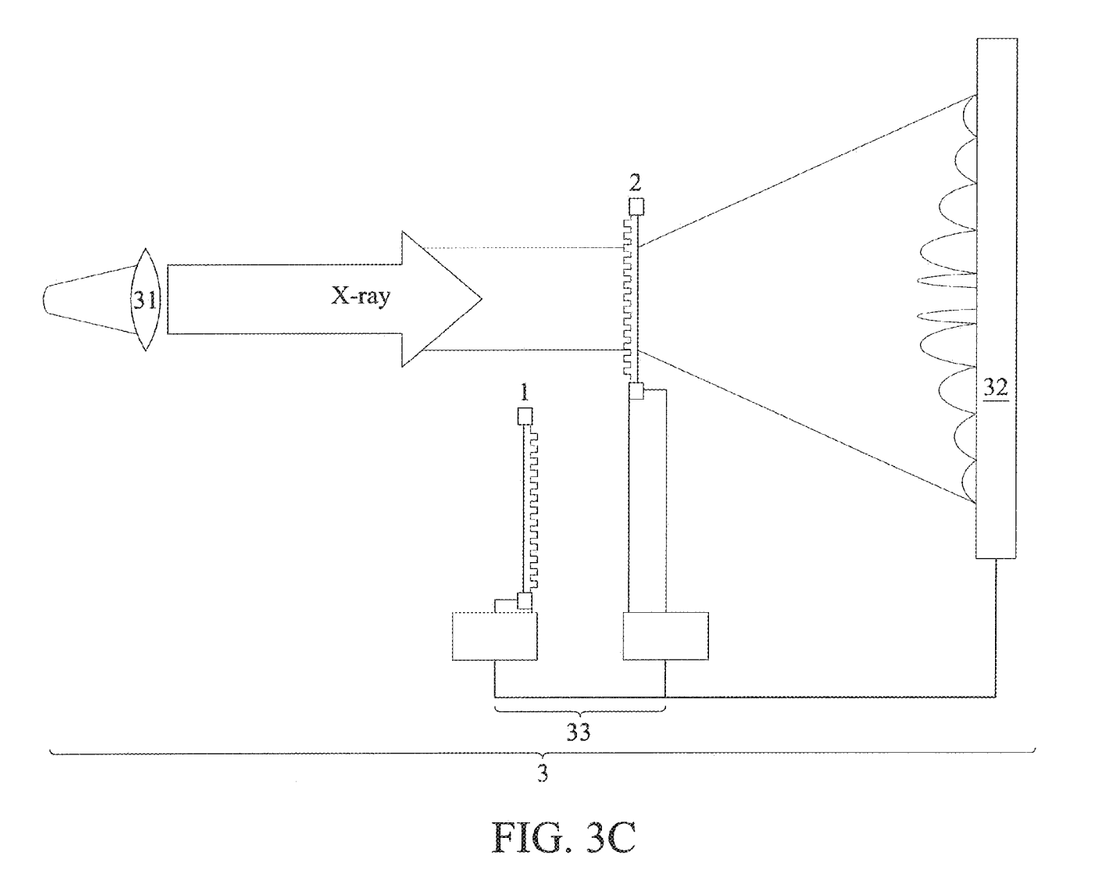

Similarly, the moving unit 33, after descending the first plate 1 and raising the second plate 2, also tilts the second plate 2 according to the first amplitude distribution of first small-angle X-ray scattering emitted from the pattern 21 of the second plate 2 impinged by the X-ray such that the second plate 2 is perpendicular to the X-ray, and rotates the second plate 2 according to the second amplitude distribution of second small-angle X-ray scattering emitted from the pattern 21 of the second plate 2 perpendicularly impinged by the X-ray, as shown in FIG. 3C.

Figure 3D:
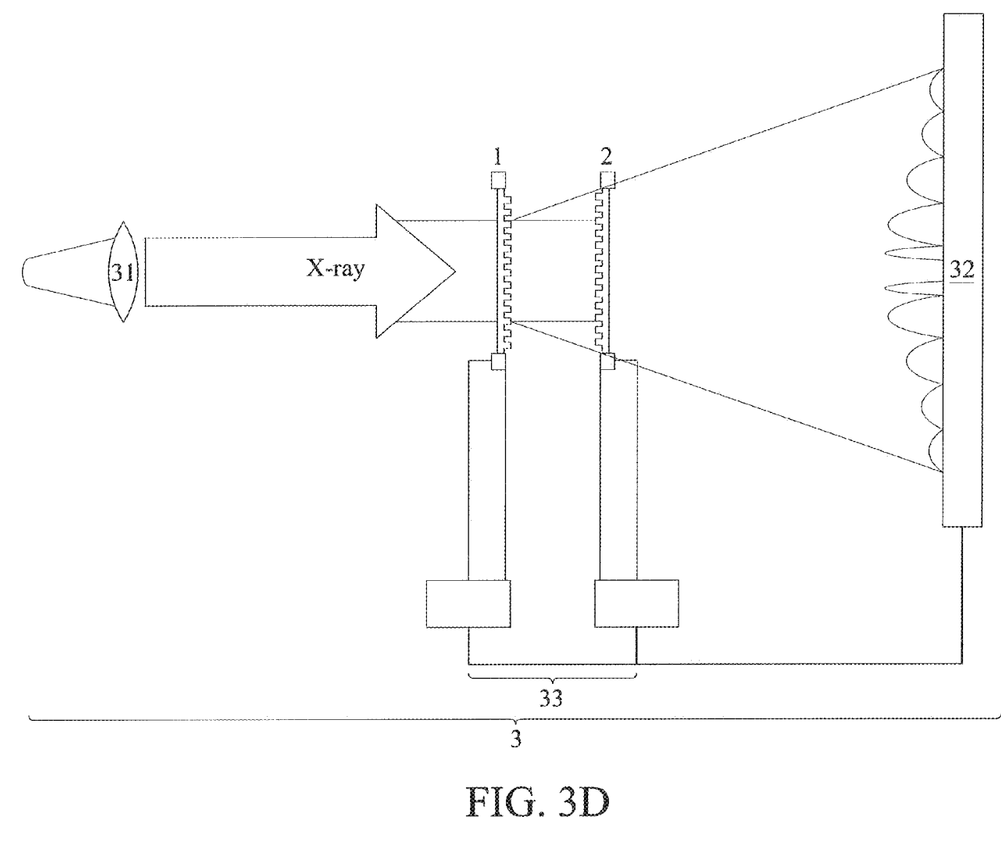
Figure 3E:
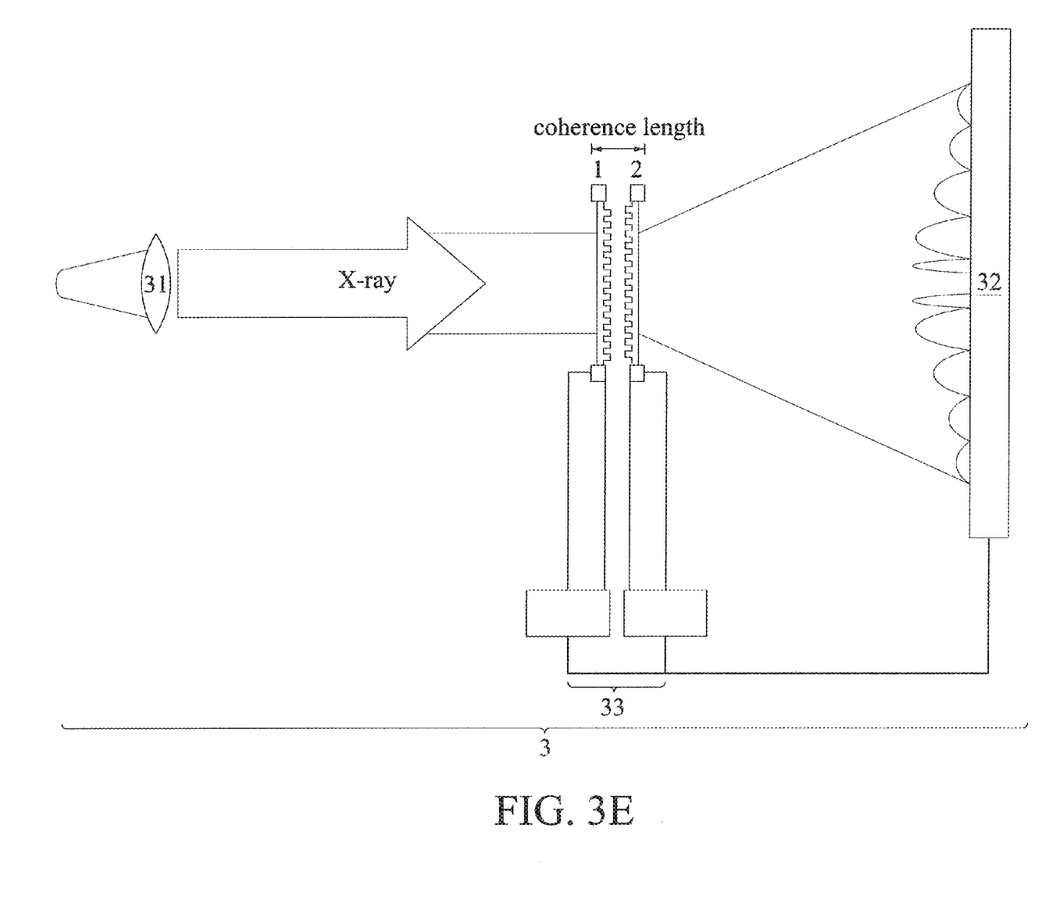

As shown in FIG. 3D, the moving unit 33 raises the first plate 1 again, with the second plate 2 resting still. The X-ray passes through the first and second plates 1 and 2, and the detector 32 detects composite small-angle X-ray scattering emitted from the patterns 11 and 21 of the first and second plate 1 and 2 perpendicularly impinged by the X-ray. The moving unit 33 aligns the first and second plates 1 and 2, for example by raising/descending the first plate 1, with the second plate 2 fixed, according to a composite amplitude distribution of the composite small-angle X-ray scattering. In an embodiment, the moving unit 33 further adjusts a distance between the first and second plates 1 and 2 to be less than a coherence length of the X-ray, as shown in FIG. 3E, to facilitate the precise alignment of the first and second plates 1 and 2. The moving unit 33 aligns the first and second plates 1 and 2 by reference to the composite amplitude distribution of the composite small-angle X-ray scattering I(q) and the corresponding ηs of FIG. 2.

Since X-ray has a shorter wavelength and better transmittance, as compared with visible or infrared red light, the method and apparatus according to the disclosure can provide accurate alignment of two nano-scale wafers. Besides, the small-angle X-ray scattering of the two wafers can be stored in a database, for quick reference of subsequent processes.

While the disclosure has been described in conjunction with a specific best mode, it is to be understood that many alternatives, modifications, and variations will be apparent to those skilled in the art in light of the aforesaid description. Accordingly, it is intended to embrace all such alternatives, modifications, and variations that fall within the scope of the included claims. All matters heretofore set forth herein or shown in the accompanying drawings are to be interpreted in an illustrative and non-limiting sense.

The invention claimed is:

1. An apparatus for aligning a first plate and a second plate that are parallel to each other and have a same orientation, the apparatus comprising:
   a detector that detects composite small-angle X-ray scattering emitted from patterns of the first and second plates that are perpendicularly impinged by X-ray; and
   a moving unit that aligns the first and second plates according to a composite amplitude distribution of diffraction peaks of the composite small-angle X-ray scattering.

2. The apparatus of claim 1, wherein the moving unit further adjusts a distance between the first and second plates.

3. The apparatus of claim 2, wherein the distance is adjusted to be less than a coherence length of the X-ray.

4. The apparatus of claim 1, further comprising an X-ray source that emits the X-ray.

5. The apparatus of claim 1, wherein the detector further detects first small-angle X-ray scattering emitted from the pattern of each of the first and second plates that is impinged by the X-ray, and the moving unit further tilts each of the first and second plates according to a first amplitude distribution of the first small-angle X-ray scattering.

6. The apparatus of claim 5, wherein the moving unit tilts each of the first and second plates to be perpendicular to the X-ray impinged thereon.

7. The apparatus of claim 6, wherein the detector further detects second small-angle X-ray scattering emitted from the pattern of each of the first and second plates that is perpendicularly impinged by the X-ray, and the moving unit further rotates each of the first and second plates according to a second amplitude distribution of the second small-angle X-ray scattering.

8. A method for aligning a first plate and a second plate that are parallel to each other and have a same orientation, the method comprising:
- detecting composite small-angle X-ray scattering emitted from patterns of the first and second plates that are perpendicularly impinged by X-ray; and
- aligning the first and second plates according to a composite amplitude distribution of diffraction peaks of the composite small-angle X-ray scattering.

9. The method of claim 8, further comprising adjusting a distance between the first and second plates to be less than a coherence length of the X-ray.

10. The method of claim 8, further comprising detecting first small-angle X-ray scattering emitted from the pattern of each of the first and second plates that is impinged by the X-ray, and tilting each of the first and second plates according to a first amplitude distribution of the first small-angle X-ray scattering such that the X-ray is perpendicularly impinged on the first plate.

11. The method of claim 10, further comprising detecting second small-angle X-ray scattering emitted from the pattern of each of the first and second plates that is perpendicularly impinged by the X-ray, and rotating each of the first and second plates according to a second amplitude distribution of the second small-angle X-ray scattering.

\* \* \* \* \*